United States Patent [19]

Accaries et al.

[11] Patent Number: 5,049,125
[45] Date of Patent: Sep. 17, 1991

[54] NEEDLELESS INJECTION APPARATUS OF A LIQUID, NOTABLY FOR DENTAL CARE

[76] Inventors: Claude Accaries, Route du Pont-Neuf, 64260 Arudy; Pierre Ibis, Lotissement Gilardi - 27 Chemin Cam-Loung, 64230 Lescar; Henri Toprides, 7 rue de Crillon, 922 10 Saint-Cloud, all of France

[21] Appl. No.: 302,233
[22] PCT Filed: May 24, 1988
[86] PCT No.: PCT/FR88/00258
§ 371 Date: Dec. 29, 1988
§ 102(e) Date: Dec. 29, 1988
[87] PCT Pub. No.: WO88/09189
PCT Pub. Date: Dec. 1, 1988

[30] Foreign Application Priority Data
May 26, 1987 [FR] France ............................ 87 07409
Apr. 11, 1988 [FR] France ............................ 88 04764

[51] Int. Cl.$^5$ .................................................. A61M 5/30
[52] U.S. Cl. .......................................... 604/70; 604/68; 604/71
[58] Field of Search .................. 604/68, 69, 70, 71, 604/72; 222/3, 389; 433/80

[56] References Cited

U.S. PATENT DOCUMENTS

| 3,130,723 | 4/1964 | Venditty | 128/173 |
| 3,189,029 | 6/1965 | Stephens | 604/70 |
| 3,425,413 | 2/1969 | Stephens | 604/71 |
| 3,461,867 | 8/1969 | Zimmer . | |
| 3,688,765 | 9/1972 | Grasaway | 604/70 |
| 4,165,739 | 8/1979 | Doherty . | |
| 4,570,832 | 2/1986 | Kroger | 222/325 |

FOREIGN PATENT DOCUMENTS

A863907 1/1962 United Kingdom .

Primary Examiner—C. Fred Rosenbaum
Assistant Examiner—Corrine Maglione
Attorney, Agent, or Firm—Roland Plottel

[57] ABSTRACT

A liquid-injection instrument without needle comprises an elongated body in two separable parts placed end to end. The first, so-called medical part, comprises at least one cavity receiving a liquid-tight cell which contains the injection liquid and has a movable base which, when displaced, forces liquid from the cell towards at least one variable-volume dosing chamber in the medical part. This communicates with a nozzle provided with an injector capable of forming a narrow jet of liquid following forcible expulsion of liquid from the dosing chamber. The second, so-called motor part, comprises a pneumatically controlled mobile assembly which effects alternating movements. The mobile assembly comprises a working piston (52-233-420) and a control and propulsion spring (62-241-444) which acts on the piston when gradually compressed by the movement of a plunger (52-276-445) caused by the pressure of the compressed air in a gas-tight chamber (51-287) in the body. The movement of the plunger continues until the spring is suddenly released and is accompanied by depressurization of the compressed air, ensuring rapid movement of the piston and expulsion of the liquid from the dosing chamber (38-243-430), after which the plunger returns to its initial position.

31 Claims, 8 Drawing Sheets

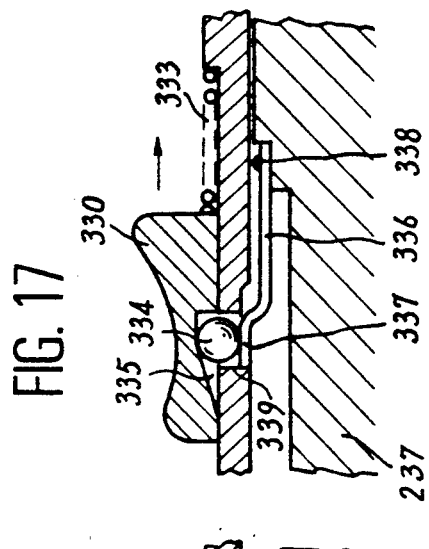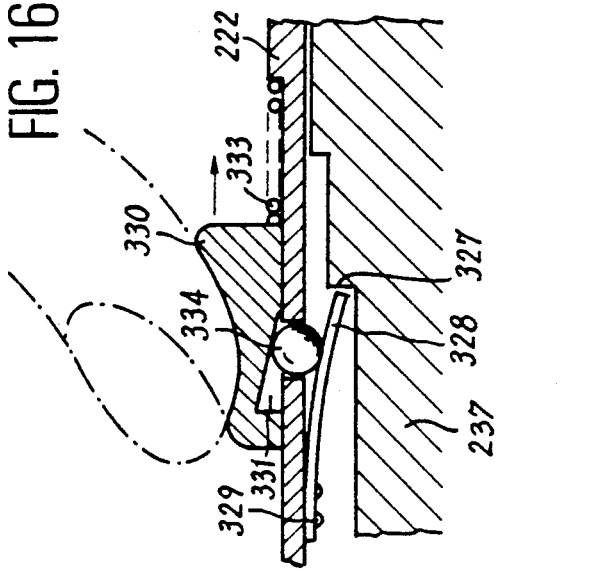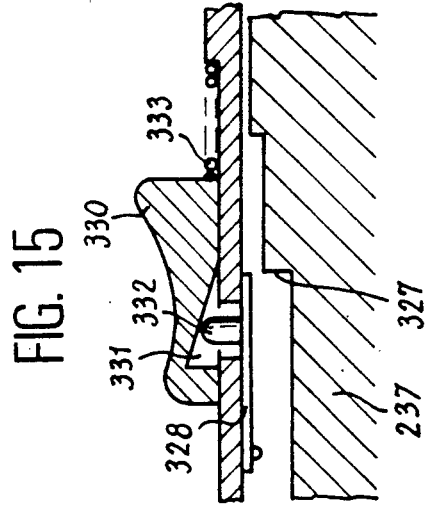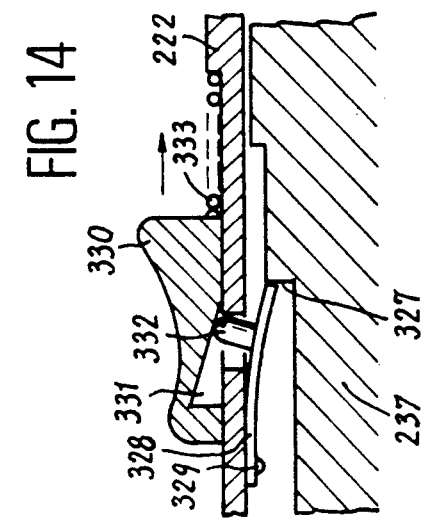

NEEDLELESS INJECTION APPARATUS OF A LIQUID, NOTABLY FOR DENTAL CARE

FIELD OF THE INVENTION

The present invention is an apparatus for the injection of liquid products inside the dental mucosa of a patient by means of a jet with a settable pressure directly penetrating the gum.

BACKGROUND OF THE INVENTION

It is known that in many interventions carried out by dental surgeons on a person, notably when giving a local anaesthesia prior to the extraction of a tooth, or more generally for the administration inside the dental mucosa of medicinal substances adapted to a determined treatment, it is necessary to inject a liquid product in a quantity which is controlled with precision, with a frequency which, eventually, can be relatively high during the intervention. To this effect, apparatus adapted to dental practice and presenting an adequate ergonomy for facilitating their handling by the practitioner are known, but their shape is nevertheless derived more or less directly from standard syringes where the liquid, pushed by a piston moving in a cavity, is driven out through the inner channel of a hollow needle, which was previously introduced via its open and cutting end into the mucosa, at the place where the product has to be injected. However, these standard apparatus are not very practical and require notably a consumption of needles the replacement of which is essential after each intervention, and even after each injection. Moreover, the use of a needle fixed at the end of a syringe always has a traumatic effect on the patient; it is borne by some of these patients only with great difficulties. On the other hand, the use of an apparatus of this kind requires from the practitioner great skill, above all if the site of the gum where the product has to be injected is not easily accessible; for example, inside and on the bottom of the buccal cavity or in the vicinity of the ligual face of the incisive teeth, the space requirement of the needle makes the operation all the more delicate because the chosen region is so difficult to reach.

Finally, there are the risks resulting from a possible contamination of the patient, and even of the practitioner, through the blood which often accompanies the penetration by the needle of the mucosa, this being another, still more important, disadvantage of using standard injection apparatus employing such needles.

In order to remedy this disadvantage, it has already been proposed to replace the hereabovementioned syringe with a needleless injector device, of the general type of those used in the care technique known as mesotherapy. However, with the corresponding apparatus, the cocking of the piston which creates the extremely fine liquid jet directly penetrating the gum due only to the force of its impact in contact with said gum is carried out by means of a manual lever which has to be operated at each injection. Hence, it is a heavy apparatus, difficult to operate, and, above all, does not allow varying the dose to be injected, which is always the same, since the piston stroke is fixed. Moreover, for the injection of larger doses, in order, for example, to carry out a deep local anaesthesia, the penetration of the useful quantity of product requires carrying out a series of successive operations of the apparatus cocking lever, which makes the apparatus neither practical nor efficient.

Finally, another disadvantage results from the fact that in some embodiments, the liquid to be injected, prior to the use of the apparatus, has to be transferred in a reservoir mounted inside the apparatus, hence causing a problem for cleaning and eventually sterilizing the latter when there is a change of product, with, moreover, the disadvantage of the waste of the product, the excess of said product normally having to be discarded each time.

OBJECTS AND SUMMARY OF THE INVENTION

The present invention relates to a needleless injection apparatus, notably for dental art applications, which remedies the disadvantages of the solutions of the prior technique, particularly by permitting the creation of a settable jet under pressure, with a repetitive cadence which can be adjusted at will. The operation of the apparatus is entirely pneumatic and controlled by a simple pressure applied by the operator himself, acting on an actuating member, for example a pedal or any similar means, to which the control console supplying compressed air which is habitually available in dental surgery installations is connected.

The apparatus according to the invention is designed in such manner that its being held in the hand of the its use, by permitting its being held in the hand of the dentist in a manner quite similar to that which he is accustomed to with his usual other instruments, of the rotary drill, water or air sprayer, etc., type, available on his working console. This is due to the design of the mechanical members of the apparatus and to their operation kinematics, which allows housing them in a cylindrical assembly of light weight, limited diameter and a very reduced total space requirement.

To this effect, the injection apparatus in consideration includes an elongated body made of two separable portions placed end to end. The first of these, called medical, includes at least one housing holding a tight cartridge containing the liquid to be injected and having a mobile bottom, the displacement of which causes the liquid to be conveyed from the cartridge to at least one dosing chamber of variable volume, formed in said first portion and communicating with a nozzle provided with an injector adapted for forming a narrow liquid jet which can abruptly deliver the liquid outside the dosing chamber. The second portion, called motive, includes a mobile assembly performing an alternating movement which is pneumatically controlled; this mobile assembly includes a working piston and a control and propulsion spring, which acts on this piston by being progressively compressed under the effect of the displacement of a pushing member, caused by the pressure of compressed air in a tight chamber provided in the body; the displacement of the pushing member continues until the moment when the spring is abruptly freed with a discharge of the compressed air pressure, thereby ensuring the rapid movement of the piston and the expulsion of the liquid outside the dosing chamber, prior to the return of the pushing member in the initial position.

In a first alternative embodiment of the apparatus in consideration, the mobile assembly includes a working piston which also plays the part of a pushing member, the piston separating the inside of the body in the second portion into two chambers disposed on either side of the working piston. The first of these is defined partially by the mobile bottom of the cartridge and is progressively set under the pressure of the compressed air in such manner so as to displace the working piston in a direction reverse to that of the control and propulsion spring housed in the second chamber, said spring causing the rapid return of the working piston after a sudden reduction of the pressure in said first chamber controlled by a distributor coaxial to the working piston and displaced over a very small distance by the piston at the end of its stroke so as to put the pressure in the first chamber in communication with the open air. During its rapid return, the working piston transmits its movement to a mobile expulsion piston in the dosing chamber, which expels the liquid out of the latter.

According to another characteristic of the apparatus in consideration, the expulsion piston of the liquid outsided the dosing chamber includes a head provided with a sealing member and slidably mounted in said chamber, said head being prolongated by a stem, possibly made of several successive elements in order to adjust the length of said stem. The expulsion piston is subjected to a permanent effect of an auxiliary spring which pushes back the stem against a coaxial end-piece, rigidly connected to the working piston and which is in contact with the end of the stem when the two portions of the body are assembled.

In another alternative embodiment, which offers the advantage of a simpler structure, and in particular a structure easier to make industrially due to a configuration of its various parts, fixed as well as mobile, which is such that it, in a general manner, revolves about the axis of the body, the working piston of the mobile assembly is subjected to the action of the control spring progressively compressed by a separated axial pushing member connected via an elastic membrane to the inner wall of a compression chamber connected to a source of compressed air. Means are provided for rigidly connecting the working piston with a temporary immobilization member provided in the body, coaxially to the piston, in such manner that beyond a determined stroke of the pushing member, causing the progressive compression of the spring, the latter is abruptly freed and causes the rapid displacement of the piston, by bringing about the expulsion outside the dosing chamber of the liquid to be injected, communicating with the cartridge forming the liquid reserve.

The mobile piston is or is not a part of an assembly which includes the cartridge as such, said cartridge being therefore immobilized inside the body or on the contrary displacable in the latter with the piston, whereby the abrupt expulsion of the liquid outside the dosing chamber toward the injection nozzle can be effected consecutively to a direct or indirect action of this piston.

Advantageously, the blocking means are constituted by balls mounted inside open housings formed in the outer wall of the piston and maintained in position by a coaxial sleeve; sliding on this wall under the effect of the pushing member, said sleeve includes a profiled recess for the escapement of the balls and the release of the piston beyond a given stroke of the sleeve.

BRIEF DESCRIPTION OF THE DRAWINGS

Other features of an injection apparatus made according to the invention, which allows bringing more completely to light the advantages it offers as compared to the prior and already known solutions in the technique, will become more apparent from the following description of several embodiments, given by way of indication and nonlimiting, with reference to the accompanying drawings wherein:

FIG. 13 illustrates an alternative embodiment of the device of FIGS. 11 and 12.

FIGS. 14 and 15 on the one hand, and 16 and 17 on the other hand, illustrate respectively and schematically other alternative embodiments of the blocking device associated with the apparatus according to the invention.

DETAILED DESCRIPTION OF THE INVENTION

Figure 1:
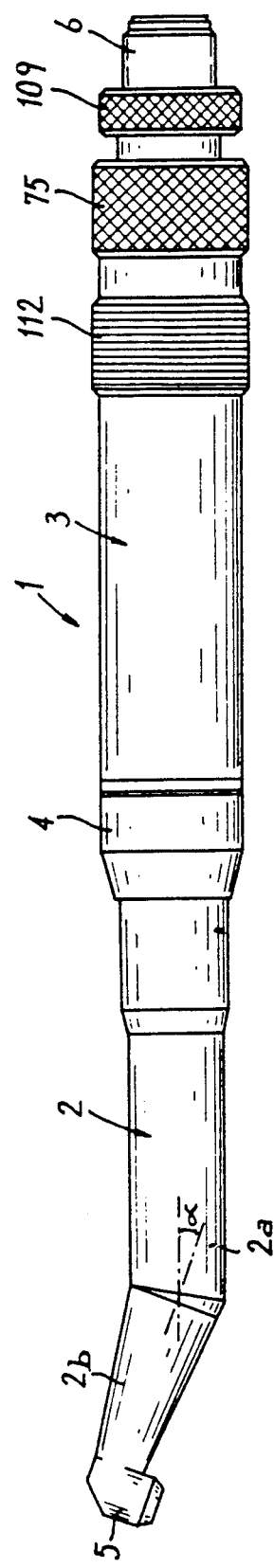
FIG. 1 is a general schematic outside view of a first embodiment of the appartus in consideration, with its two portions assembled.

The apparatus according to the invention, as is shown in FIG. 1 from the outside, includes substantially an elongated body 1 made of two separable portions 2 and 3, connected to each other when operating by a threaded connection ring 4. Portion 2 of the body, called medical portion, is formed of two elements, respectively 2a and 2b, the first of which being situated in the axis of the second portion 3, called motive portion, while element 2b is oriented in an axial direction forming with that of element 2a an angle of 10 to 15 degrees, facilitating the use of the apparatus for the practitioner who can introduce it more or less deeply in the mouth of the patient according to the position where he wishes to carry out an injection of liquid. Portion 2b includes at the end furthest from portion 2a a head 5, provided with an injection nozzle adapted for forming in the manner which will be indicated below a very thin and powerful jet of liquid, the conformation of which allows it to penetrate directly the patient's gum without the use of any needle or similar element. Opposite head 5, the motive portion 3 of body 1 includes a connection fitting 6 with a source of compressed air of a standard use in consoles of dental surgery installations. The pressure of the compressed air supplied is generally set between 2 and 7 bars.

Figure 3:
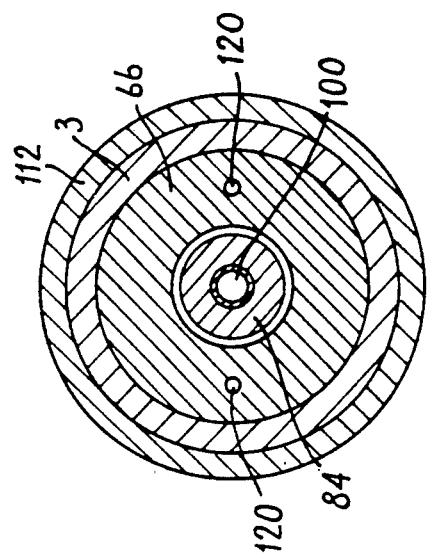
FIG. 3 is a sectional view of FIG. 2, along line III—III of the latter.
Figure 2A:
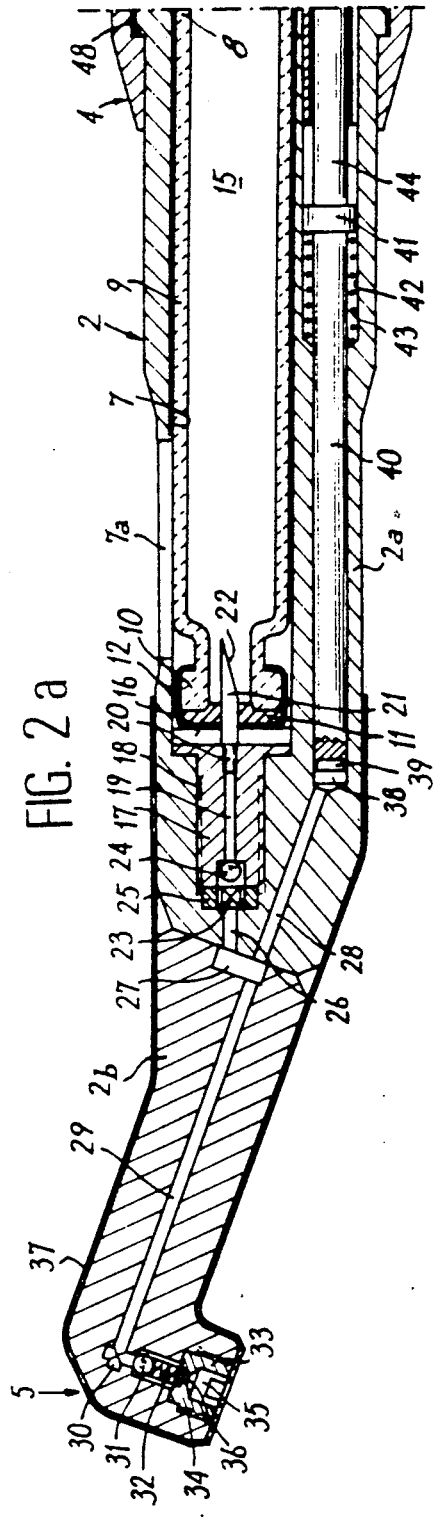
FIGS. 2a and 2b are longitudinal sectional views at a larger scale of the apparatus according to FIG. 1, illustrating more particularly the detail of the mechanical design of the two portions of the apparatus body, in order to explain the operation of said apparatus.
Figure 2B:
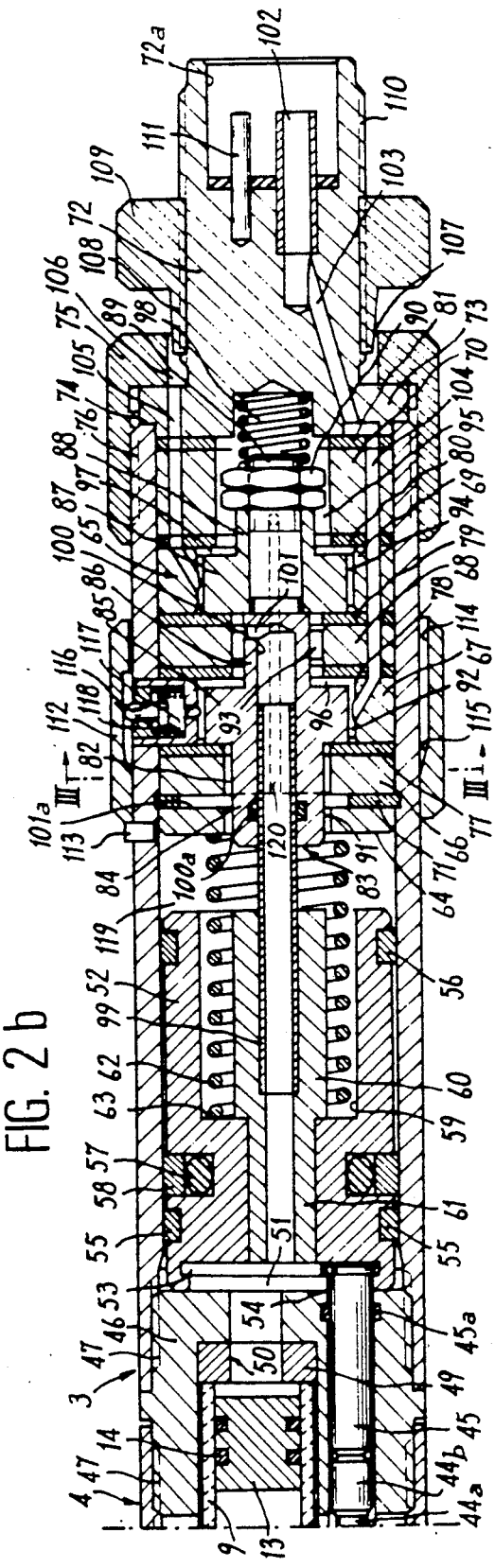

FIGS. 2a, 2b and 3 illustrate in more detail the structure of the two portions 2 and 3 of body 1 of the apparatus.

As can be seen in FIG. 2a, portion 2 is also formed with an inner housing 7, inside which can be engaged a cartridge or container of a standard type 8, presenting notably an envelope 9 inside which is enclosed a quantity of liquid which one wishes to inject in the gingival mucosa of a patient according to an exactly determined dose by using the apparatus in consideration. Envelope 9 of cartridge 8 is formed, at its end which is turned toward the bottom of housing 7 when the cartridge is introduced in the latter, a contraction defining a neck 10 on the edge of which bears a flexible plaquette 11, in rubber or any other material of the same kind, closing tightly the envelope 9. The flexible plaquette 11 is immobilized on neck 10 in known manner by a crimping capsule 12, formed with a hole in its center. At its opposite end, the envelope 9 includes a cylindrical bottom piece 13, provided in its side surface with sealing rings 14, said bottom piece 13 being capable of moving inside envelope 9 to cause progressively, as its displacement proceeds, the discharge from the cartridge of a given quantity of the liquid 15 it contains, through an outlet passage previously provided in the sealing plaquette 11. A window 7a is conveniently formed in the wall of portion 2, facing housing 7, for checking the remaining quantity of liquid in the cartridge.

Cartridge 8 thus mounted in housing 7 is bearing against the bottom of the latter on member 17, screwed by means of a transverse slot 16 formed on the end of said member in a tapped hole 18 provided in portion 2a of element 2, in alignment with the housing. Through member 17 extends a duct 19. At the end of the latter which is turned toward the inside of housing 7 is fitted or forcibly engaged the threaded end 20 of a trocar 21, thereby puncturing the sealing plaquette 11 of the cartridge via its cutting bevelled edge 22 when said cartridge is introduced inside housing 7. At its opposite end, duct 19 opens into a widened cavity 23, defined in a hollow bearing ring 25 and in which is freely mounted a ball 24, forming a closing valve for said duct when the ball is immobilized against the outlet of said duct under conditions which will be disclosed hereafter. Cavity 23 preferably has a square, triangular or other section, so that when ball 24 bears against its end on ring 25, the passage extending through the latter is not completely closed, allowing the liquid drawn from the cartridge according to the process which will be described later to flow through the cavity 23 and ring 25. Said cavity 23 is on the other hand connected via a connection channel 26 opening into a recess 27 formed in portion 2b of element 2 at the level of the zone where said element is connected to portion 2a. This recess 27 communicates on the other hand, in portions 2a and 2b respectively, with two connection ducts 28 and 29, placed in the prolongation of one another and allowing the conveyance to the injection head 5 of a determined quantity of liquid drawn from cartridge 8 and sent toward the head with the pressure necessary to this injection.

In head 5, duct 29 is connected to an element 30 bent at a right angle, at the end of which is mounted a second valve, made once again of a ball 31 applied on the end of bend 30 by a spring 32. The spring bears at the opposite end on the rear of a removable nozzle 33, screwed into the inner thread of a blind housing 34, these dispositions allowing an easy change of the nozzle when worn out or deteriorated. Nozzle 33 includes an axial recess 35 and at the bottom of said recess an injector 36 made of a icroplaquette in ruby or other very hard material particularly resistant to abrasive effects caused by the jet of liquid under pressure, this microplaquette being formed axially with a calibrated hole of very small diameter, ranging from a few hundreths to a few tenths of a millimeter according to the dimension of the jet required, and the nature of the liquid to be injected.

Preferably, a protection cap 37 in a plastic or other material surrounds the end of element 2b of portion 2, said cap having, in alignment with the nozzle 33, an appropriate opening in order not to impede the outlet of the jet supplied by the nozzle. Cap 37 is interchangeable and can be particularly easily discarded after each use of the apparatus or each procedure on a patient.

Duct 28, opposite the hereabove described duct 29, opens in turn inside element 2a in a dosing chamber 38 for the liquid to be injected. In chamber 38 is mounted a lip seal 39 fixed at the end of the head of a piston 40, called expulsion or delivery piston, arranged in such manner that according to the direction of its displacement in chamber 38, a volume of liquid is respectively sucked or expelled from the chamber. The piston head 40 includes on the other hand in its median portion a shoulder 41, slidably mounted in a counterboring 42 provided inside portion 2 of body 1 on the side of housing 7 and in which is housed a spring 43 bearing on the one hand against the bottom of counterboring 42 and on the other hand underneath shoulder 41, in such manner that the piston head 40 is permanently pushed back in the direction of portion 3 of body 1. Piston head 40 is prolongated beyond shoulder 41 by an axial stem 44, possibly made of several elements 44a, 44b, etc., of various lengths in order to adjust the total size of stem 44, and this in order to allow, as will be seen hereafter, the setting of the suction volume of liquid in dosing chamber 38, and, according to the length of the stem, modifying this volume as a function of the dose to be injected at each operating cycle of the piston and of the nature of the liquid used. Stem 44, the length of which is thus adapted, comes in abutment via its end opposite to shoulder 41 against a terminal end-piece 45, coaxial with the stem and slidably mounted in an appropriate bore formed in the closing member 46. A seal 45a ensures the tightness of end-piece 45 in piece 46. The latter includes a double outer thread 47 allowing on the one hand fixing it on the top of portion 3 of body 1 which it thus seals closed, and on the other hand screwing on it the ring 4 connecting the two portions 1 and 2 (FIG. 1). Ring 4 is stopped in translation on portion 2 by a protruding flange 48 provided on the outer surface of said portion, thereby providing by screwing the ring coupling the two portions until a final abutment against one another.

The closing member 46 caps the end of the cartridge 8 when the two portions 2 and 3 of body 1 are thus connected to one another via ring 4. Inside said member is mounted a thrust washer 49 through which extends an axial passage 50 allowing the compressed air, introduced under pressure in the first chamber 51 situated in portion 3 of body 1 behind member 46, to exert a determined presure on mobile bottom 13 of the cartridge so as to cause the delivery outside of the cartridge of a definite quantity of liquid which collects in the dosing chamber 38 in the manner which will be disclosed later.

The chamber 51 formed behind the closing member 46 is on the other hand defined in the motive portion 3 of body 1 by means of a working piston 52 forming a pushing piece as will be seen later and which is formed, notably on its opposite face, with a hollow groove 53, adapted for receiving head 54 of end-piece 45 so as to rigidly connect said end-piece to working piston 52 by ensuring in particular that the displacement of this end-piece is effected at the same time as that of piston 52. The latter includes outside rings 55 and 56 and, in the open side groove, a flexible seal 57 applying a pad 58 against the inner surface of portion 3 of the body so as to provide for the permanent tightness of chamber 51 whatever the displacements of piston 52. Piston 52 includes in its face opposite to groove 53 and therefore in its face turned to the rear of body 1, an inner recess 59 in the axis of which is mounted a hollow fitting 60, prolongated by an extention 61 forcibly driven inside the piston. Fitting 60 and its extention 61 are axially bored in order to allow the feeding of chamber 51 with compressed air.

Between fitting 60 and the inner wall of recess 59 is mounted a strong control and propulsion spring 62, bearing on the one hand against an inner bearing surface 63 provided in the bottom of recess 59 inside piston 52, and on the other hand agaisnt a bearing face 64 of a support block 65, secured against motion inside portion 3. Block 65 is formed of a succession of cylindrical rings respectively placed against each other 66, 67, 68, 69 and 70, successively engaged by force or slidingly inside body 1. The first ring 66 is immobilized in position by a circlip 71. At the opposite, the last ring 70 includes an axial prolongation 72 protruding outside portion 3 at the end of body 1, said prolongation 71 including a shoulder 73 coming in abutment against the corresponding end 74 of said portion 3, and thereby enclosing the latter. The blockage of the assembly of rings of support block 65, once put in position in body 1, is provided by means of a ring 75 screwed on an outer thread 76 formed on the surface of portion 3 (FIGS. 1 and 2b).

Between rings 66 to 70 of the support block 65 are on the other hand mounted flat seals, designated in the drawing by the successive reference numerals 77, 78, 79, 80 and 81, the first seal 77 being mounted between rings 66 and 67; the second 78 between rings 67 and 68 and so forth.

The support block with its rings and its flat seals includes also a stepped axial passage 82, designed notably for mounting inside the fixed block 65 of mobile distributor 83.

Distributor 83 is formed, for mounting reasons, in the block of two successive joint pieces, the first including a cylindrical portion 84 prolongated by an extension of larger diameter 85, in turn ending in a narrow cylindrical prolongation 86. The second portion of distributor 83 includes likewise a cylindrical portion 87, in turn prolongated to the rear of body 1 by an extention 88, the assembly being threaded onto an axis 89 and then blocked on said axis by a double nut 90.

The mounting of distributor 83 inside the passage 82 of the support block 65 defines thus, between the various rings of the block and the corresponding portions of the distributor, successive annular clearances, designated in the drawing by reference numerals 91, 92, 93, 94, the end-piece 72 forming axially a blind housing 95 around nut 90. Moreover, the arrangement of the various elements is such that there is provided, in the position of distributor 83 which is shown in FIG. 2b, an axial clearance 96 left free between the cylindrical extension 8 and the flat seal 78 on the one hand, and an axial clearance of same width 97 between the cylindrical portion 87 and the flat seal 80. These clearances 96 and 97 which respectively communicate with clearance 92 and 94 define notably the possible and limited stroke of distributor 83. Thus, when due to the displacement of the distributor to the rear of body 1 inside support block 65 in passage 82, clearances 96 and 97 disappear, portions 85 and 87 come in engagement with the flat seals 78 and 80, and simultaneously identical clearances appear, respectively 96a and 97a (FIG. 4) between these same cylindrical portions 85 and 87 and the flat seals 77 and 79.

A spring 98 provided inside housing 95 of end-piece 72 behind distributor 83 allows exerting a return force permanently on the latter directed from the right to the left in the drawing, thereby tending to return the distributor to the position shown in FIG. 2b where exist clearances 96 and 97, while clearances 96a and 97a are on the contrary suppressed.

The axial fitting 60 of piston 52 includes a connection tube 99 slidably mounted inside a bore 100 formed axially in distributor 83, with the interposition of an O-ring 100a on which can slide tube 99.

Bore 100 of distributor 83 communicates via a radial duct 101 with the annular clearance 93 provided between the prolongation 86 and the fixed ring 68. At the end of body 1, the end-piece of the support block 65 is formed on the other hand with an open recess 72a into which opens a tubing 102 establishing the connection with a source of compressed air having a pressure between 2 and 7 bars, available in a standard manner in the console of dental surgery apparatus. Tubing 102 is connected inside piece 72 to a duct 103 prolongated by a connection duct 104 extending successively through rings 70, 69 and 68 prior to opening through ring 67 into the annular clearance 92. Likewise, through rings 69, 70 and end-piece 72 is also provided a second duct 105 connecting the annular clearance 94 with a cavity 106 open to the outside and formed at the rear of portion 3 of body 1. Cavity 106 has its opening or annular outlet slot 107 partially closed by a conical portion 108 provided at the end of a ring 109 (FIGS. 1 and 2b) adapted to be screwed onto a thread 110 provided on the outer surface of end-piece 72. The progressive screwing of ring 109 allows its conical portion 108 to more or less penetrate cavity 106 and thereby vary the opening of clearance 107.

The equipment of the apparatus is completed by including in cavity 72a formed at the end of end-piece 72 a guiding pin 111 permitting the connection of compressed air inlet tubing 102 to an appropriate channel. Moreover, body 1 is advantageously provided with a safety member, constituted by a sliding ring 112, mounted mobile between two positions on the outer surface of portion 3, one of which is defined by an abutment on a fixed stopping shoulder 113. Ring 112 includes inside it a recessed passage 114, ending into a slanting face 115. According to the position of ring 112, slanting face 115 acts or does not act on head 116 of a safety valve 117 subjected to the action of a spring 118 and arranged according to whether ring 112 keeps it inside portion 3 of body 1 or on the contrary permits it to protrude out of this portion, so as to connect clearance 92 with the air or to maintain it closed, inside which opens the end of this valve. Finally, between chamber 119 situated on the opposite side of piston 52 as regards chamber 51 and housing 95, is provided at least one communication duct 120 (in fact two ducts are visible in FIG. 3).

The operation of the above needleless injection apparatus is the following: during the first step, the apparatus is prepared by placing in the housing, inside portion 2 or medical portion of body 1, which is then separated from portion 3, a cartridge 8, containing a liquid 15 which one wishes to inject inside the dental mucosa of a patient in one or preferably several successive injections. Once the cartridge is in position, it is pressed against the bottom of the housing so that trocar 21 punctures via its cutting and bevelled edge 22 the sealing washer 11 and makes it possible, under the effect of a pressure exerted on the mobile bottom 13 of the cartridge, for the liquid 15 to flow through duct 19 toward cavity 27 and from there via ducts 28 and 29 respectively, either to the injection nozzle 33 or to the dosing chamber 38. Once portion 2 is thus equipped, it is assembled with portion 3, or motive portion, by the appropriate screwing of ring 4. This operation permits notably the end of stem 44 prolongating the delivery piston head 40, which is pushed back by spring 43 acting against shoulder 41, to be maintained in permanent contact with the corresponding end of end-piece 45, rigidly connected to piston 52 in portion 3 thus connected to portion 2. It should be noted that the apparatus is arranged for allowing the adjustment of the initial setting of the volume of dosing chamber 38, by adjusting the length of stem 44 which can be modified at will by adding or removing one or several of the elements 44a, 44b, etc., which, placed end to end, prolongate the stem in the manner already indicated.

The apparatus is then ready to operate. It is sufficient in practice, while holding it in a hand, to press a pedal or any other similar control means for starting the admission turbine of compressed air to the apparatus, so that this air arriving through tubing 102 be conveyed by duct 103 and clearance 92 to distributor 83 which, in the initial position, is such as shown in FIG. 2. The compressed air under pressure flows through the radial clearance 96, then is separated through the annular clearance 93 and from there in the connection radial duct 101, by being thus brought to the axial bore 100 of the distributor. Through the latter, it flows thrugh the connection duct 99, then into chamber 51 and finally through passage 50, and it exerts its pressure against the mobile bottom 13 of cartridge 8 on the one hand, and against the opposite face of the working piston 52. Simultaneously, chamber 119 situated on the other side of piston 52 is set in communication with housing 95 by the connection ducts 120 (FIG. 3) and it is, under these conditions, set in communication with the open air through the radial clearance 97, the annular clearance 94, duct 105, cavity 106 and the settable outlet slot 107.

The pressure of the compressed air thus admitted to chamber 51 causes the displacement of the mobile bottom 13 of cartridge 8 by pushing out of the latter the quantity of liquid 15 which is just necessary for filling, after passing through ring 25, duct 26, recess 27 and air duct 28, the dosing chamber 38 and this, as the volume of the latter increases under the simultaneous displacement of piston 52 which, via end-piece 45 with which it is rigidly connected, allows stem 44 and therefore the head of delivery piston 40 to move from the left to the right in the drawing of FIG. 2b. During this displacement, the liquid 15 is sucked outside cartridge 8 through trocar 21, cavity 23 and duct 28, fills the dosing chamber, the valve-forming ball 24 being pushed back from duct 19. On the contrary, the liquid cannot escape through the injection nozzle 33 since the access to the latter is prevented by ball 31 of the second valve being applied against the end of bend 30 by spring 32.

Figure 4:
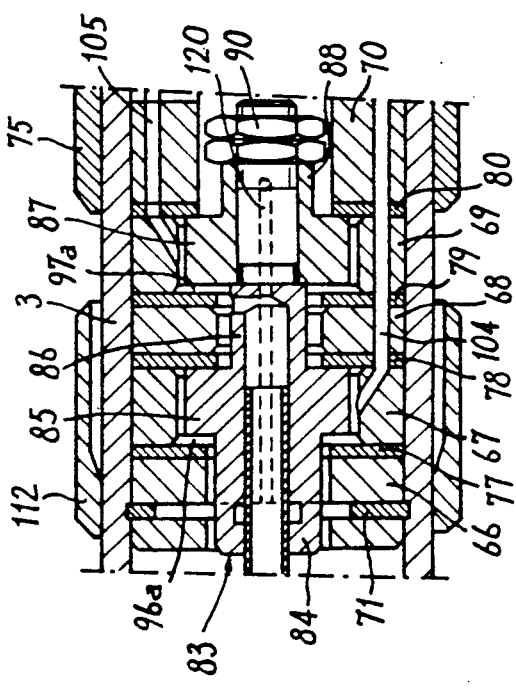
FIG. 4 is a detailed view of FIG. 2b, showing the displacement of the distributor.

As long as the pressure of the compressed air in chamber 51 is maintained, the displacement movement from the left to the right in the drawing of FIG. 2b of working piston 52 forming a pushing member goes on inside the motive portion 3 of body 1, the tightness during this displacement between chambers 51 and 119 respectively being maintained by rings 55, 56 and pad 58. During this movement, the control and propulsion spring 62 is progressively tensed in chamber 119 which communicates with the open air via ducts 120, clearance 97, 93, duct 105 and slot 107, until fitting 60 comes in contact with the end of portion 84 of distributor 83 which is slightly protruding inside said chamber. At that moment, piston 52 which continues its stroke acts on distributor 83 which it slightly pushes back by removing the radial clearances 96 and 97 and creating simultaneously clearances 96a and 97a (FIG. 4). The extensions 85 and 87 of the distributor abandon their engagement with seals 77 and 79 of support block 65 and come in contact with seals 78 and 80.

Simultaneously, chamber 51 is set in communication with the open air, the compressed air it contains being set directly in communication via bore 100, radial duct 101, annular clearance 93 and radial clearance 97a with duct 105, cavity 106 and slot 107. Under these conditions, the control and propulsion spring 62, previously compressed during the preceding step, can abruptly spring back by forcefully returning the working piston 52 from the right to the left of the apparatus in FIG. 2b. During this movement, end-piece 45, connected to piston 52, transmits its displacement to stem 44 and, via the latter, to the head of the delivery piston 40 which expels with a pressure multiplied by the surface ratio of these pistons the liquid previously sucked into the dosing chamber 38. The volume of liquid thus delivered flows then via ducts 28 and 29 to the injection head 5, where it pushes back ball 31 against its spring 32 and flows through the microplaquette 36 of nozzle 33 which projects it in the pattern of a very thin and powerful jet beyond cavity 35. The injection head 5 having been previously put by the practitioner on the site where the injection has to be made, the jet thus produced directly penetrates the mucosa of the patient, according to a process which is well known per se in the mesotherapy technique. The liquid delivered from chamber 38 cannot return to cartridge 8 since the ball 24 of the first valve, being subjected to the delivery pressure, is applied against the end of duct 19 which it seals closed.

The apparatus is designed in such manner that after the control and propulsion spring 62 and the return of the working piston 52 to its initial position, a control device (not shown) cuts the admission of compressed air, which can be delivered again to the apparatus only by a new control action of the practitioner acting on the proper pedal. Thus, the apparatus avoids a continuous sequential operation which would present the severe risk of producing uncontrolled successive injections of liquid, particularly before the nozzle is placed on the precise site where each of the injections have to be made. As an alternative, by pressing the pedal with the foot in order to give an impulsion, the distributor can be displaced toward the left by piston 52 bearing on it. The distributor remains then in this position for a certain period because of the difference of pressure between the left hand side face and the right hand side face of the distributor. Therefore, jerks of the apparatus are avoided in this position.

On the other hand, the sliding ring 112 allows the practitioner to manually control the operation of the apparatus, while permitting the actuation of the injection head only under exactly defined conditions and avoiding notably an injection of liquid caused by pressure inadvertently applied on the pedal while the injection head is still not properly placed opposite a gum in the desired region. As long as ring 112 is not in fact brought to its abutment position against stopping ring 113, the slanting face 115 of passage 114 bears on hand 116 of safety valve 117, setting in a permanent way the annular clearance 92 in communication with a free exhaust, so that the compressed air brought by ducts 103 and 104 in this clearance 92 escapes directly to the outside without being able to exert its pressure in chamber 51 and to displace the working piston 52, cocking the injection head. On the contrary, once the nozzle 33 is brought exactly in contact with the gun in the desired site, the practitioner, by pushing back ring 112, sets the apparatus in an operative state; any pressure on the pedal will then, according to the process described, ensure the filling of the dosing chamber and then the formation of the injection jet through the effect of the abrupt return caused by the delivery spring.

As is already apparent from the preceding description, the setting in operation of the injection apparatus according to the invention offers many advantages. In particular, the apparatus affords by a simple setting of the threaded ring 109 mounted at the rear of the motive portion 3 of body 1 the ability to adjust according to requirements the dimensions of the discharge slot 107 for the compressed air and therefore creating in chamber 119 an adjustable counter-pressure opposing the movement of the working piston 52. According to the nature of the liquid to be injected and to the conditions of its use, particularly the depth inside the dental mucosa to which the liquid has to be injected, the practitioner can thus adjust in the most simple and rapid manner the operation of his apparatus by a simple rotation of ring 109. This ring in fact also has at the level of its portion 108 penetrating housing 107 a reference index, graduated directly with indications characterizing the strength of the jet created and/or the depth of the injection which can be obtained by the latter.

The constitution of stem 44 in several elements of determined respective lengths for adjusting the useful volume of the dosing chamber allows modifying at will the quantity of liquid injected at each stroke of the working piston through the injection nozzle. The presence of window 7a in front of housing 7 in the medical portion 2 of body 1, where an appropriate index can also be engraved, affords the control at any moment of the quantity of available remaining liquid and notably warns the practitioner of the forthcoming exhaustion of cartridge 8. The replacement of the latter once it is empty by a new one which is full and contains the same liquid or another can also be carried out easily, by separating the medical portion 2 from the motive portion 3 after having unscrewed ring 4, removing the empty cartridge and replacing it with a new cartridge placed inside the housing on the point of trocar 21.

The outer shape of the apparatus is especially designed in such manner that it is practically identical to that of the other intervention tools at the disposal of the practitioner on his working console; in particular, the body 1 can be easily held in the hand in the manner of a writing pen, preferably at the level of the break formed between the two elements 2a and 2b of the medical portion 2, the medical portion 3 resting in the hollow formed between the thumb and the index, this hold allowing a great precision in the positioning of the injection head inside the buccal cavity of a patient. Due to a relief (not shown) machined around body 1, one can also provide the apparatus with an antiskid outer surface facilitating its hold in the hand, thus avoiding the risks that the apparatus moves or slips during the injection operation.

Another decisive advantage of the apparatus in consideration is its perfect asepsis, particularly at the level of the injection head 5. The mounting all around the latter of a protection cap 37 notably allows avoiding that any possible emissions of blood or saliva from the patient pollute the apparatus, said cap 37 being discardable after each procedure on the patient. On the other hand, the design of the apparatus in two separable portions, respectively a medical portion and a motive portion, allows, before each use on a different patient, an efficient sterilization of the medical portion, which is disassembled from the motive portion and placed in an autoclave or any similar apparatus, with ultraviolet radiations for example. The motive portion, which is never in contact with the patient's mouth, can be used as is.

Figure 5:
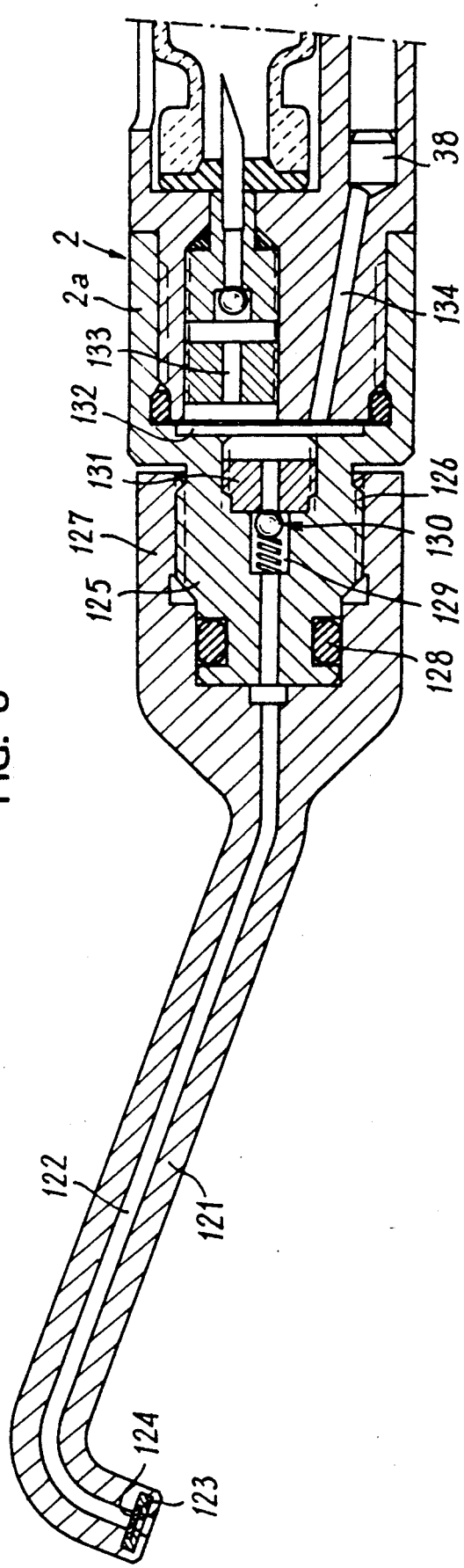
FIG. 5 is a detailed view of an alternative embodiment of the end of the apparatus carrying the injection nozzle.

Because of the design of its various portions, the apparatus has a reduced weight and space requirement, added to a facility of use which is quite agreeable and allows, without difficulty, placing the injection head properly in contact with any part of the dental mucosa in the region where an injection should be made, even in the most awkward positions, for example on the lingual face of the incisive teeth or in the bottom of the mouth in the vicinity of the palate. Eventually, the injection head 20 can be modified in order to make it narrower and more slender in its anterior portion penetrating the buccal cavity. Thus, it can be made in the manner shown in FIG. 5 where the end of element 2b of the medical portion 2 is prolongated by an end-piece 121 of very small diameter, removable and interchangeable, provided only with an axial duct 122 which opens directly in a cavity 123 formed at its end in contact with the region where an injection under pressure has to be made, and in the bottom of which there is mounted a flat injector 124. In this alternative embodiment, the valve which should close duct 122 in order to avoid the escape of the liquid from the cartridge during the filling phase of the dosing chamber is no longer placed in the vicinity of the injector 124 but in an element 2a of portion 2 of the body in a prolongation 125 of the latter, on which is screwed via an inner thread 126 a sleeve 127 provided at the end of the end-piece 121, opposite to that where the injector 124 is, the tightness of the mounting being provided by a seal 128. Of course, other modes of fixation of sleeve 127 on prolongation 125 could also be envisaged, for example by a ball catch or a bayonet latch, whereby the version of the apparatus thus provided is more directly adapted to the case where, due to new standards or law regulations, it would be necessary to discard or sterilize after use any element having penetrated the patient's mouth, because of concern for the safety and protection of the persons treated as well as of the practitioner.

Duct 122 opens into a chamber 129 where there is disposed a ball valve 130, forming a channel extending through a ring 131 screwed in a corresponding housing. In portion 2a forms a recess 132 in which there is open at the same time a duct 133 connected to the cartridge through an assembly similar to that already described with reference to FIG. 2a, and another duct 134 connecting the recess 132 to dosing chamber 38.

Figure 6A:
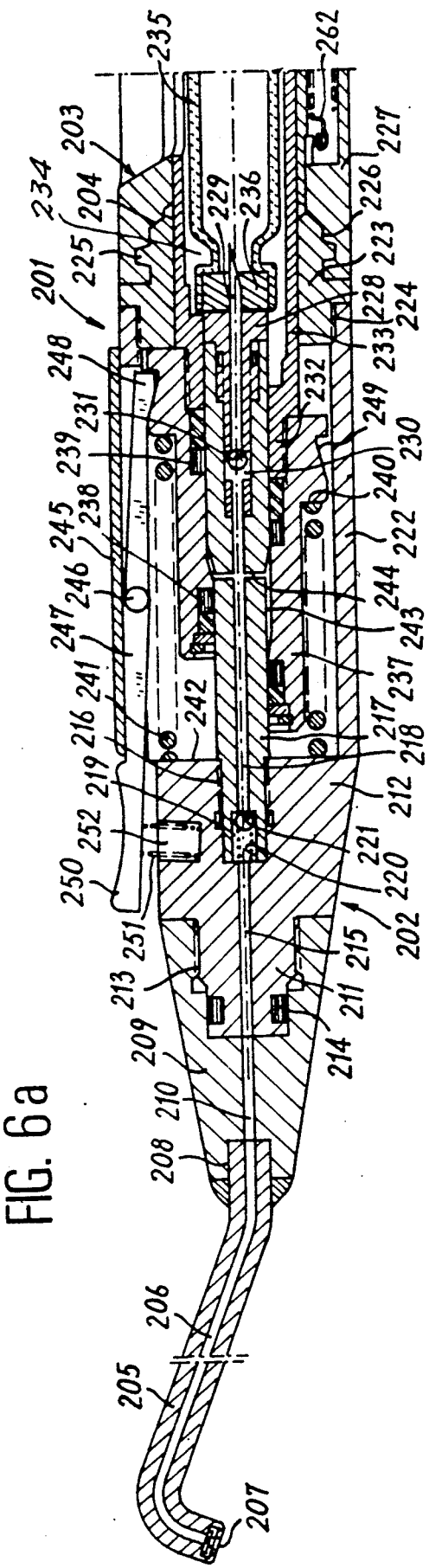
FIGS. 6a and 6b are views of two connecting portions of the apparatus according to the invention, as per another alternative embodiment.
Figure 6B:
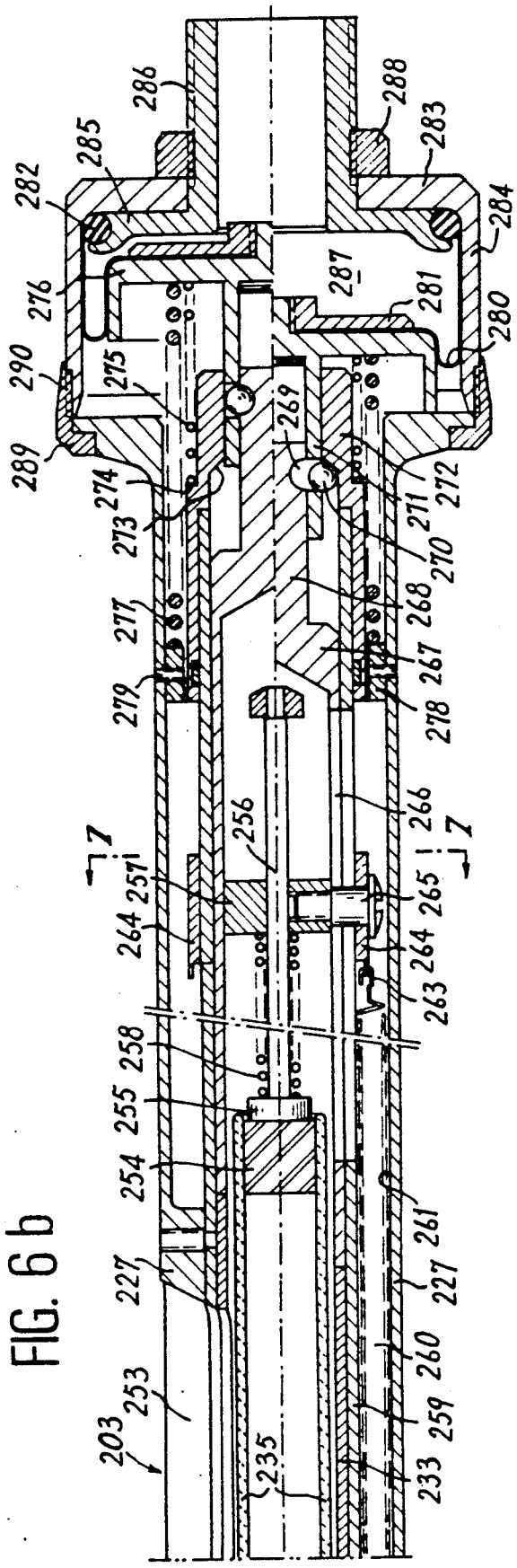

In FIGS. 6a and 6b which, placed side by side, illustrate a longitudinal section of another embodiment of the apparatus in consideration, reference numeral 201 designates the body of this apparatus, made as in the previous sample of two coaxial portions, respectively 202 and 203, the first which is called medical portion being adapted to be coupled to the second portion, called motive portion, by means of a rapid connection system 204 of the quarter of a turn type or other.

At its end situated on the left side in the drawing, portion 202 includes a terminal spout 205, thin and elongated, including a feeding chanel 206 for an appropriate injection liquid to an end nozzle 207. On the opposite side, spout 205 is driven into a housing 208 provided at the end of a support 209 including an axial channel 210 placed in the prolongation of channel 206. Said support 209 is in turn mounted in the end 211 of an intermediate member 212 on which it is screwed at 213 with the interposition of a seal 214. Channel 210 is prolongated in turn by a channel 215 in said intermediate member 212 which also includes a thread 216 receiving a chuck 217, in turn formed axially with a duct 218 in the axis of channel 216 and being connected to the latter via a ball valve 219 subjected to the action of a spring 220 in such manner that under the effect of the spring, ball 221 closed normally at the end of duct 218.

The intermediate member 212 is prolongated to the right side of the drawing by an outer sleeve 222 surrounding the chuck 217, said sleeve being rigidly connected to an end plug 223 screwed at 224. Plug 223 includes protruding ribs 225 adapted to fit into grooves of same profile 226 for forming at the end of a sleeve of same diameter 227 which prolongated sleeve 222 the rapid connection system 204 between the two portions 202 and 203 of the apparatus body.

At its end opposite to spout 205, chuck 217 includes a closing end-piece 228 allowing the mounting in the axis of duct 218 of a needle or trocar 229. The latter can also be closed by a valve mounted in a cavity 230 of the chuck comprising a ball 231 adapted to close the corresponding extremity of the trocar.

About chuck 217 is slidably mounted the tubular end 232 of a hollow sleeve 233 defining inside a housing 234 inside which is mounted a cartridge 235 having its end turned toward the spout 205 closed by a plug 236. The latter is, prior to the use of the apparatus, punctured by the end of trocar 229 so as to allow, under conditions which will be made clear later, the flowing of a liquid contained in this cartridge through trocar 229 and then beyond the latter, in duct 218 as long as ball 231 frees the passage necessary for this flow.

On the tubular end 232 of sleeve 233 is mounted a mobile and hollow piston 237, adapted for sliding on chuck 217, annular seals 238 and 239 mounted inside the piston ensuring the tightness. Piston 237 is formed with a transverse bearing surface 240 for a control spring 241 bearing on the opposite side against an abutment face 242 provided on the intermediate member 212. The mobile piston 237 defines thus, with the fixed chuck 217, an annular chamber 243 which constitutes the dosing chamber for the product drawn from cartridge 235 and conveyed to this chamber via at least one transverse passage 244 provided in the chuck. On the outer sleeve 222 is applied and fixed an outer cap 245 on which is articulated about an axis 246 a lever 247, provided at one end with a heel 248 adapted to block in position the mobile piston 237 by being engaged in an opened housing 249 of said piston. On the opposite side of heel 248, lever 247 is formed with a control shallow formation 250 for the finger of the user which allows tipping the lever about its axis against a spring 251 mounted in a housing 252 of the intermediate member 212, said tipping motion thereby freeing the heel 248 from housing 249.

Sleeve 227 includes a port 253 for visualizing directly cartridge 235, through the body of the apparatus, in particular when the latter is made of a transparent plastic material, so as to follow the evolution of the level of liquid which it contains, as injections of successive doses are carried out, the evacuation of the liquid being accompanied by a displacement of the sliding bottom 254, on the opposite side of plug 236, said bottom 254 being subjected to the action of the head 255 of a piston stem 256, slidably mounted through a guiding support 257 by being subjected to the permanent action of a spring 258.

Figure 7:
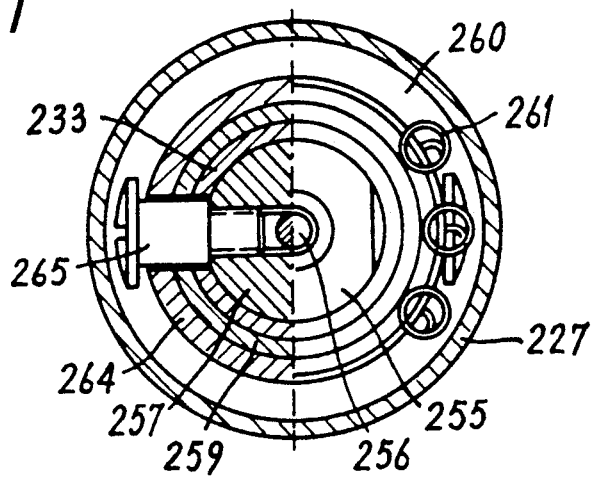
FIG. 7 is a transverse sectional view at a slightly larger scale along line II—II of FIG. 6b.

Between the hollow sleeve 233 and the outer sleeves 222 and 227 is mounted a guiding tube 259, defining with sleeve 227 a space 260 in which are mounted springs 261, regularly distributed about the axis of said sleeve and fixed at their respective ends at 262 on sleeve 227 and at 263 on a cylindrical washer 264, rigidly connected by a transverse screw 265 to the guiding support 257 through an opening 266 formed laterally in sleeve 233 and tube 259 (FIG. 7).

At its upper portion, sleeve 233 includes an end-piece 267, prolongated by a terminal portion 268, formed with opened grooves 269 adapted for receiving several balls 270 mounted in said groove so as to block in position the portion 268 with respect to a coaxial tube 271. The guiding tube 259 includes also a prolongation 272, capping from the outside tube 271 and immobilizing the balls 270. The prolongation 272 has a bearing surface slanting to the outside 273 and outside a shoulder 274 for a return spring 275, bearing on the opposite side against a flange 276 forming an axial pushing member, extending transversely at the end of the coaxial tube 271. Another spring 277 is mounted outside tube 259 and bears also against the flange 276, the latter being stopped on the opposite side by a washer 278 blocked by screws 279 against the inner surface of sleeve 227.

The flange 276 is associated with a sealing membrane 280 immobilized against the upper face of the flange by a support plaquette 281, said membrane being terminated by a bead 282 kept captive between the bottom 283 of an end plug 284 provided at the end of the apparatus and a clamping member 285 provided with a tubular prolongation 286 allowing introducing in the body of the apparatus, behind membrane 280, a convenient pressure of compressed air in a chamber 287, thus defined. The end plug 284 is immobilized on the tubular prolongation 286 by a screw 288 and is also maintained by a ring 289 rigidly connected to the sleeve 227 in which is screwed the plug 284 via an inner thread 290.

Figure 8:
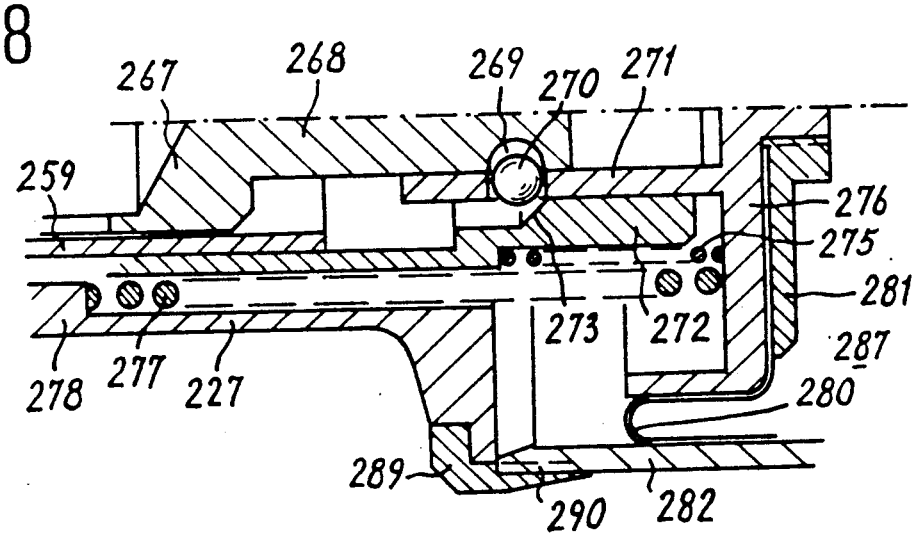
FIGS. 8 and 9 are partial longitudinal sectional views, at a larger scale, of the members while blocking, and then the disengagement of the apparatus working piston to the effort exerted on the latter by the pushing member, which is in turn actuated by a controlled pressure of compressed air.
Figure 9:
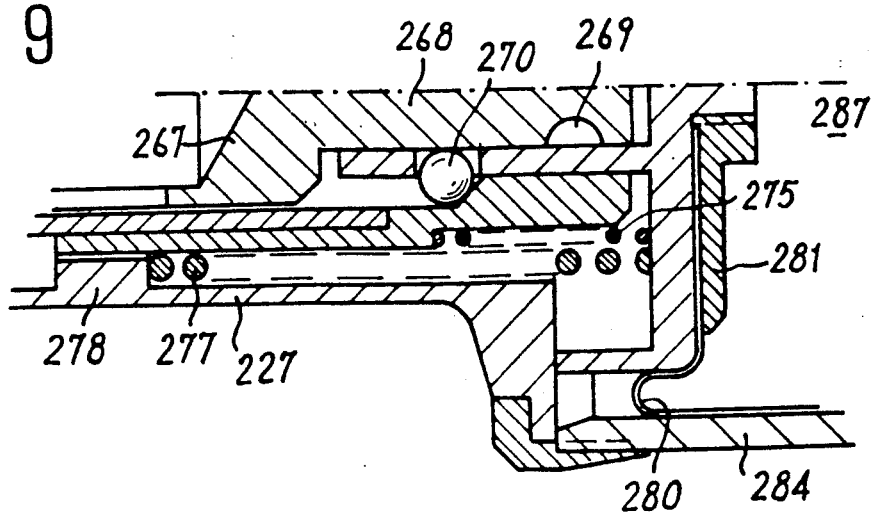

FIGS. 8 and 9 allow, in connection with FIGS. 6a and 6b, to better illustrate the manner in which the apparatus is used in the hereabove described embodiment, where the assembly constituted by members 237, 233, 267, 268 form notably the working piston, the flange 276, the tube 271 and the membrane 280 constituting the pushing member.

In order in particular to proceed to an injection of a given dose of liquid through nozzle 207 previously positioned in the vicinity of the site where this injection should be made, the user, during the first stage, frees by lever 247 the piston 237, by disengaging the heel 248 of said lever from housing 249. At that moment and by an appropriate control, for example exerted with the foot, he introduces via the tubular prolongation 286 a convenient pressure of compressed air in the compression chamber 287. Under the effect of this pressure, the assembly formed by flange 276 and tube 271 moves and drives simultaneously via the end portion 268 the sleeve 233, causing in turn the displacement of piston 237 against spring 241.

During this movement, the dosing chamber 243 is progressively filled with liquid sucked from cartridge 235 by trocar 229, duct 218 and the transverse passages 244, the flow of liquid being made possible by the displacement of ball 231 in housing 230 which frees the open end of the trocar.

This movement is pursued, notably until the balls 270, which rigidly connect tube 271 of the terminal endpiece 268 of the motive piston, come in front of the slanting bearing surface 273 of prolongation 272, allowing then the escapement of said balls outside their housing 269. At that moment, the working piston 237 is abruptly freed, spring 241 brutally pushing back the mobile assembly in the reverse direction. Simultaneously, the liquid contained in the dosing chamber 243 is expelled from the latter through the passages 244 and the duct 218 under the effect of the pressure, ball 221 which normally closes duct 218 being pushed back against its spring 219, thereby allowing the escapement of the liquid toward the successive ducts 215, 210 and 206 to the injection nozzle 207. At the same time, ball 231 comes back and closes the end of trocar 229, thereby avoiding the return of liquid to the cartridge.

In the terminal phase of the movement, springs 275 and 277 bring back flange 276 to the initial position, with the return of balls 270 in their housing 269 in order to again rigidly connect tube 271 and the end portion 268, the apparatus being thus ready for a new cycle of operation.

Figure 10:
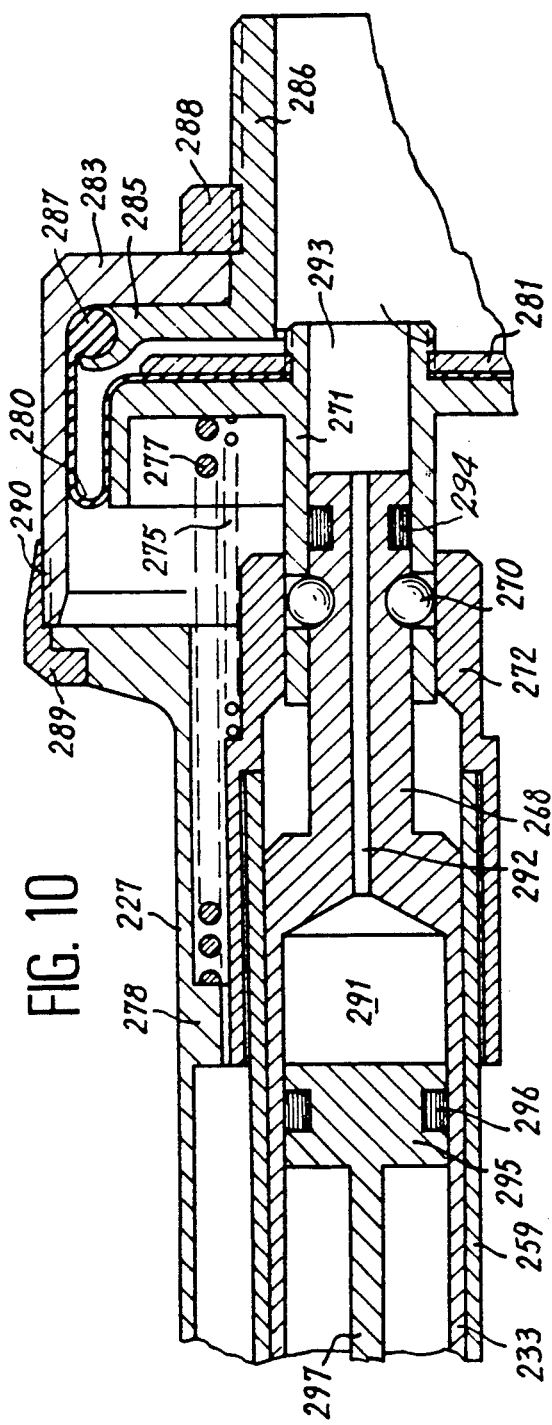
FIG. 10 is another partial sectional view of the alternative embodiment of the operational means for exerting on the liquid contained in the apparatus cartridge the pressure necessary for the flow of said liquid toward the dosing chamber.

FIG. 10 illustrates an alternative embodiment of the apparatus shown in FIGS. 6a and 6b, as regards the means for exerting on bottom 254 of cartridge 235 a convenient pressure, whatever the filling degree of said cartridge, as the operating cycle of the apparatus goes on, with the formation at each shot through the injector 207 of a fine jet of liquid under pressure.

In this alternative embodiment, prolongation 268 of hollow sleeve 233 which slides inside tube 271 defines on the side of the cartridge a tight chamber 291, connected by an axial duct 292 extending through the prolongation 268 to the opposite portion of tube 271, in turn in communication via the tubular prolongation 286 with the outer source of compressed air, causing, in the hereabove described manner, the displacement of the pushing member. An annular seal 294 is carried by the prolongation 278 and is in contact with the inner surface of prolongation 272. In chamber 291 is mounted a piston 295, also carrying an annular seal 296 in engagement with the inner surface of hollow sleeve 233, 268, said piston 295 being connected by an axis 297 to the bottom 254 of the cartridge. In this alternative embodiment, it is therefore directly the pressure of air in chamber 291 which is exerted on piston 295 and which is permanently transmitted to bottom 254, by transmitting to the liquid in the cartridge a thrust which is maintained constant to itself each time the control air pressure is admitted in the apparatus. The device is thus equivalent to that described in reference to FIGS. 6a and 6b, bringing in action springs 261 and the guiding support 257.

In the first embodiment previously envisaged, the apparatus can be set in operation only if the user has previously tipped the blocking lever 247, by exerting on the control shallow formation 250 a limited effort against spring 251, thereby disengaging heel 248 of the lever and freeing the hollow sleeve 233.

Figure 12:
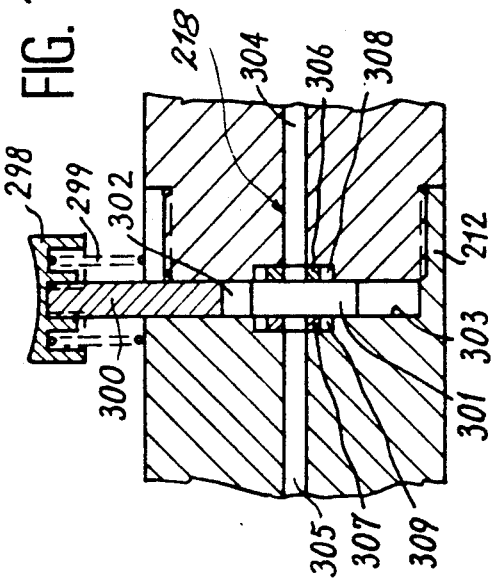
FIGS. 11 and 12 are respectively transverse and longitudinal sectional views of an alternative embodiment of a device for immobilizing the working piston until the apparatus has been conveniently set in position, prior to effecting the injection of a liquid jet.
Figure 11:
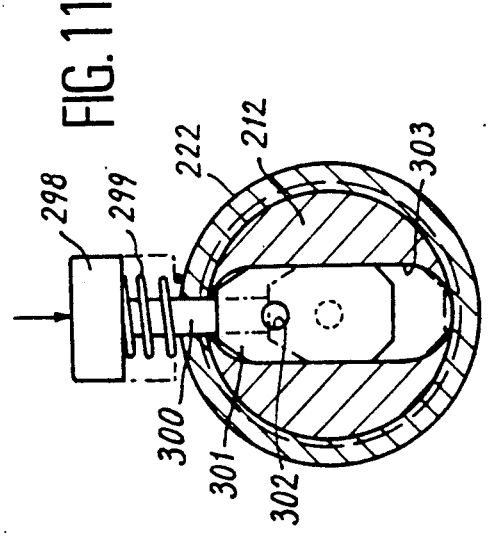

FIGS. 11 and 12 illustrate another alternative embodiment which, without intending this time to block the hollow sleeve, nevertheless prevents the escape of the liquid outside the annular chamber 243, and allowing therefore once again but in a different form the creation of the jet at the outlet of the injector only when the apparatus has been previously properly positioned, the user only then authorizing the operating cycle.

In this alternative embodiment, the device for provisionally preventing the operation is made of a knob 298, normally pushed back upwardly with respect to body 222 by a spring 299, said knob including a stem 300 rigidly connected to a transverse plaquette 301 formed with a central hole 302. The plaquette is mounted so as to slide vertically under the effect of knob 298 inside a housing 303 provided in the intermediate member 212. As can be easily conceived when looking at FIGS. 11 and 12, when knob 298 is in a released position, the transverse plaquette 301 closes the communication between the two portions 304 and 305, respectively situated on either side of duct 218, seals 306 and 307 being advantageously provided on each side of the counterborings 308 and 309 receiving them in front of the plaquette in housing 303. On the contrary, if the user exerts on knob 298 an effort directed downwardly against spring 299, he brings hole 302 in register with the two portions 304 and 305, thereby providing the continuity of duct 218 prior to the flow of the liquid drawn from chamber 243 and the discharge under pressure of this liquid to injector 207.

FIGS. 13 to 17 illustrate other alternative embodiments of the means capable to prevent in various forms the operation of the apparatus, as long as the latter is not brought to a proper position with injector 217 being in the immediate vicinity of the site where the jet of liquid should be directed.

In the example shown in FIG. 13, the intermediate member 212 is formed with a transverse hole 310 for the mounting of radial pins 311, each being subjected to the action of a spring 312 bearing against a protruding head 313 and tending to push these pins back to the outside of the slot, by disengaging the shell 314 of a plunger 315 provided with a seal 316 in its outer surface and slidably mounted in a housing 317 of the intermediate member 212. Plunger 315 includes an end pin 318 adapted for blocking in the closed position ball 221 of the valve, which closes thus the end of duct 218. The same plunger is subjected to the action of a spring 319 bearing on a fixed plaquette 320 mounted in the portion in register of the end piece 211, with interposition of a seal 321.

In the alternative embodiment in consideration, the intermediate member 212 is associated with a sliding thumb-piece 322, formed with an outer shallow formation 323 allowing the user to slide it freely on the outer surface of the member by bringing the heads 313 of pins 311 in register with an annular recess 324, thereby allowing said pins to escape to the outside, thus freeing heel 314 and therefore plunger 315 and ball 221. The sliding thumb-piece 322 is permanently returned to the latching position of pins 311 by a spring 325 mounted in a housing 326 between the outer sleeve 222 and a bearing surface of said thumb-piece so that if the operator releases his pressure on the spring, the latter brings the thumb-piece back to the position so the heads of pins 311 are returned to the inside, thereby locking plunger 315 once again.

In the alternative embodiment ilustrated in FIGS. 14 and 15, an assembly is shown which is substantially equivalent but simpler, the intermediate member 212 being formed with an outer shoulder 327 forming an abutment for the end of a spring blade 328 rigidly fixed by a rivet 329 on a sliding thumb-piece 330. This thumb-piece 330 includes an inner recess 331 inside which can move a teat 332 provided at the end of blade 328 according to the axial position of the thumb-piece on the outer sleeve 222. A spring 333 is mounted behind the thumb-piece in order to return it to its initial position.

In FIG. 14, the thumb-piece 330 is such that the narrow portion of housing 331 pushes back the teat 332 to the inside, blade 328 blocking the intermediate member 212 under such conditions and therefore the whole of the elements forming the pushing member of the apparatus, due to the bearing of shoulder 327 on blade 328.

In the position shown in FIG. 15, thumb-piece 330 is pushed back against spring 333, thereby allowing the pins 332 to escape into the wider portion of recess 331, the spring blade 328 being disengaged from shoulder 327 and thereby freeing member 212.

In FIG. 16, the alternative embodiment shown is equivalent to that envisaged hereabove, teat 332 being here replaced by a ball 334, thereby facilitating the displacement of the thumb-piece by being driven in housing 331.

In FIG. 17 a similar arrangement is shown, in which ball 334 can retract in a recess 335 of thumb-piece 330 having a profile reverse to that of the previous examples, the spring blade 336 being this time fixed by a rivet 338 to the intermediate member 212, said blade being shaped in such manner that its free end 337 is bent so as to come in abutment against a bearing surface 339 formed in the outer sleeve 222.

Figure 18A:
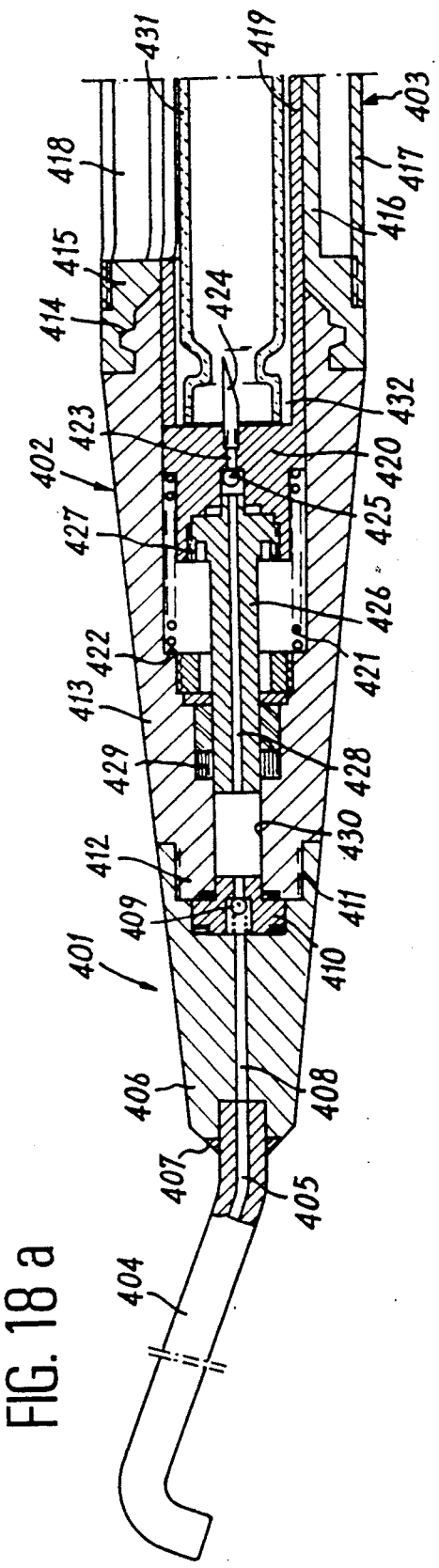
FIGS. 18a and 18b show the two consecutive portions of the apparatus according to another general alternative embodiment of said appartus.
Figure 18B:
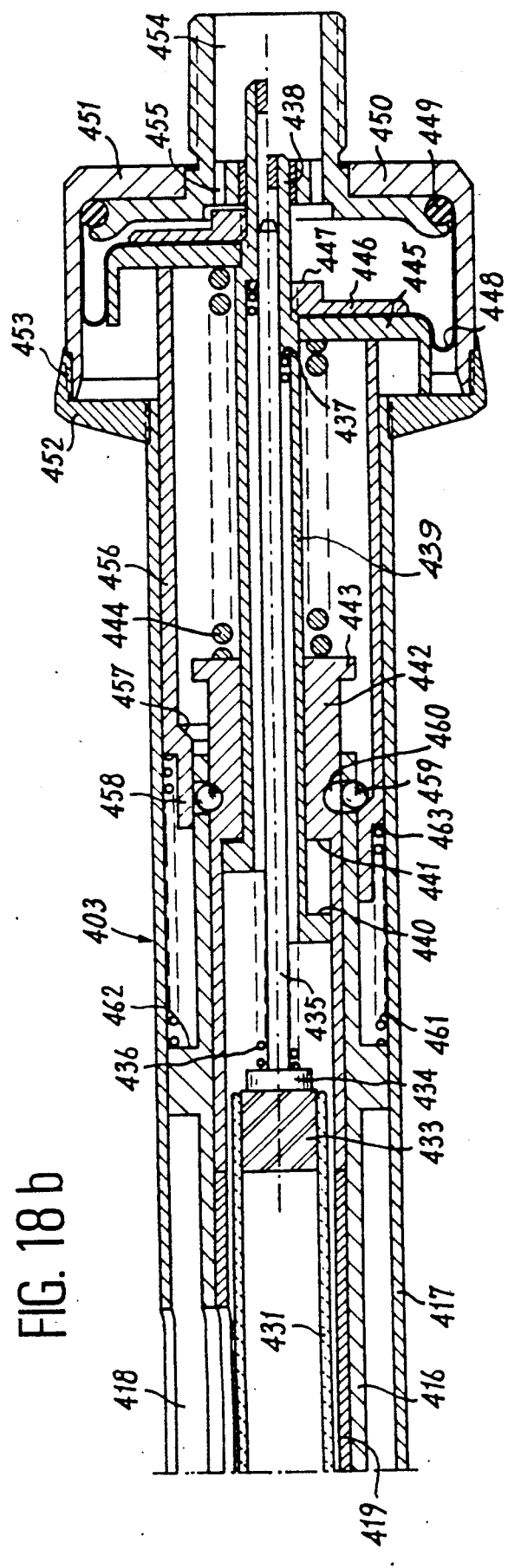

FIGS. 18a and 18b show another alternative embodiment of the apparatus according to the invention, arranged in such manner that, contrary to the first embodiment where the liquid is drawn from the cartridge into the annular dosing chamber when the pushing member returns to its rear position, this suction is effected here during the return motion of chuck 426 via return spring 421 prior to the pushing member being abruptly freed so as to produce the desired jet through the end injector.

In this alternative embodiment, the apparatus includes, as previously, a body 401 formed of two coaxial portions, respectively 402 and 403. The inner portion 402 includes an end spout 404 supporting at its end the injector (not shown) and formed with an inner duct 405. It is connected to an end portion 406 by means of an appropriate connection 407. In said member 406 is formed a duct 408 provided with a ball valve 409 mounted in a support member 410. Member 406 is connected via a thread 411 to the end 412 of an intermediate member 413. At the opposite, the latter is provided with a rapid coupling member 414, with a fitting 415 provided at the end of a tube 415 which is in turn coated by an outer sleeve 417. A side window 418 is formed in the sleeve in a similar manner to the arrangements already envisaged in the first embodiment.

Inside tube 416 is mounted a hollow sleeve 419, tube 416 at one end is turned with a spout 404, and at the other end has a piston 420. A return spring 421 is provided between the piston 420 and a bearing surface 422 formed in the itnermediate member 413. Inside piston 420 is formed a duct 423, prolongated on one side by a needle or trocar 424 and closed at the other side by a ball valve 425, provided facing a chuck 426 including an axial duct 428, whereby said chuck can be displaced in contact with a seal 429 mounted in the inner surface of a housing 430 formed in member 413.

Needle 424 punctures the end plug of cartridge 431 mounted in the inner region 432 defined between the hollow sleeve 419 and piston 420.

At its opposite end, cartridge 431 is closed by a mobile bottom 433, permanently subjected to the thrust of a piston 434 rigidly connected to an axial stem 435, a spring 436 being mounted between piston 434 and a bearing surface 437 and the cylindrical prolongation 438 of a tube 439.

Said tube 439 is formed with a flange 440 mounted mobile inside the hollow sleeve 419 and adapted for coming to bear against an inner flange 441 provided in an end-piece 442 formed at the end of said sleeve. End-piece 442 includes a flange 443 forming a bearing surface for a strong spring 444, which is in turn applied by its opposite end against a flange 445 secured against motion on prolongation 438 of tube 439 by a ring 446, which is in turn screwed on a threat 447 in the outer surface of prolongation 438. An elastic membrane 448 is secured against motion between flange 445 and ring 446, said membrane including an end bead 449 maintained between flange 450 and a cover 451. Finally, the latter is secured against motion with regard to sleeve 417 by a ring 452 screwed at 453.

In FIG. 18b the compressed air intake has been shown at 454 in the apparatus, where the air can flow through cover 451 via passage openings 455 in order to exert on flange 445 an appropriate effort. The tightness during the displacement of the pushing member of the apparatus is provided by membrane 448. Flange 445 is prolongated by a tubular member 456, mobile coaxially inside the outer sleeve 417. Said member 456 includes in its inner surface a slanting bearing surface 457 and a cylindrical prolongation 458, sliding in contact with the outer surface of hollow sleeve 416 in contact with the blocking balls 459 maintained captive in housings 460 formed in the end portion 442 of sleeve 419. A spring 461 is mounted between a fixed bearing surface 462 of tube 416 and a shoulder 463 of tubular member 456.

In this third embodiment, the operation of the apparatus is the following: when the user has brought the apparatus in the precise vicinity of the site where an injection of liquid has to be made, the apparatus being provided with a latching device similar to one of those previously described in any one of FIGS. 6 to 17 but not shown here, he controls via a foot contact, for example, the intake of air which, through openings 455, exerts on flanges 450-445 and forming a piston a corresponding thrust, by compressing during a first stage the control spring 444. During this movement, tube 439 moves with the flange, by applying an effort on piston 434 and bottom 433 of cartridge 431 via spring 436. The corresponding pressure disengages ball 425 from duct 423 and allows the liquid from the cartridge to fill housing 430 forming a dosing chamber, chuck 426 remaining in a fixed position due to the thrust in the reverse direction exerted by spring 421.

Simultaneously, tubular member 456 moves with flange 445 and compresses spring 461.

At the end of the stroke, tubular member 456 presents its slanting bearing surface 457 to balls 459 and allows the latter to escape to the outside, between end portion 442 and the tubular member. End portion 442 and therefore the hollow sleeve 419 to which it is rigidly connected are abruptly freed, with spring 444 previously compressed by the movement of flange 445 abruptly springing back and pushing back sleeve 419 and with it piston 420 and chuck 426. Valve 425 closes back while valve 409 opens and allows the liquid accumulated in housing 430 to be totally and abruptly expelled by ducts 408 and 405 to the injector mounted at the end of spout 404.

During the following phase, the pressure of air being released, springs 421 and 461 return the assembly of mobile parts to their initial position, the abutment of flange 445 against flange 450 allowing the end-piece 442 to move alone at the end of the stroke, until balls 459 are returned in register with their housings 460 into which they are then pushed back, thereby latching again the end-piece and tube 416 until a new operation cycle is started.

Of course and as is apparent from the preceding, it goes without saying that the invention is not limited only to the embodiments specially envisaged hereabove; on the contrary, it encompasses all the variants thereof. In particular, one could, without modifying the operation kinematics of the apparatus and its possible features previously described, provide for example in the medical portion, two and even three dosing chambers placed parallel to each other inside the body, each of them being associated with a delivery piston actuated simultaneously with the others by the working piston, in order to produce at the level of the head, provided with as many adjacent injectors, two or three parallel jets, adapted to penetrate at the same moment the mucosa to be treated. Likewise, in other alternative embodiments, one could envisage to associate to a single dosing chamber and to a single injector connected to the latter, two housings in the body, each containing a cartridge with a different liquid, with an inverter allowing connecting one or the other to the dosing chamber, and this so as to provide the successive injections of said liquids without having to dismantle the apparatus and to change the cartridge it contains. Finally, one can provide on the practitioner's working console a control assembly giving him, at any moment, information on the injection pressure, the number of injections made, the volume of these injections, etc.

We claim:

1. A needleless liquid injection apparatus which includes an elongated body comprising first and second separable portions, said first separable portion (2), here also called medical portion, comprising at least one housing (7) adapted to receive a tight cartridge (8), said tight cartridge (8) comprising a movable bottom piece (13) and containing a liquid (15) to be injected, said first separable portion (2) further comprising at least one dosing chamber (38) in communication with said housing (7) and comprising a delivery piston (40), and a nozzle (33) in communication with said dosing chamber (38), said nozzle (33) comprising an injector (36) adapted for forming a narrow liquid jet upon abrupt delivery of liquid from said dosing chamber (38), said second separable portion (3), here also called motive portion (3), comprising a tubing connection (102) and an assembly adapted to perform a pneumatically controlled alternating movement, said assembly comprising a working piston (52) adapted for alternating motion between first and second piston positions, a control-and-propulsion spring (62) disposed to act on said working piston (52) in a first direction, an end piece (45) adapted to communicate the motion of said working piston (52) to said delivery piston, a distributor (83) adapted for alternating motion between first and second distributor positions, means (98) for preferentially positioning said distributor (83) in said first distributor position, a tight chamber (51) which, when said distributor (83) is in said first distributor position, is in pneumatically pressurizing communication with said tubing connection (102) and which, when said distributor (83) is in said second distributor position, is pneumatically disconnected from said tubing connection (102), pressure in said tight chamber (51) acting in said first direction on said bottom piece (13) and in a second direction opposite to said first direction on said working piston (52), said working piston (52) and said distributor (83) being disposed relative to each other such that, upon movement of said working piston (52) under the influence of pneumatic pressure, said working piston (52) comes into contact with said distributor (83), whereby said distributor (83) assumes said second distributor position, thereby interrupting pressurization, thereby permitting said working piston (52) to move in said first direction by action of said control-and-propulsion spring (62), and thereby causing abrupt delivery of liquid from said dosing chamber (38).

2. Apparatus according to claim 1, comprising an auxiliary spring (43) disposed to act on said delivery piston (40) in said second direction.

3. Apparatus according to claim 1, comprising a trocar (21) which is disposed in said housing (7) such that, upon insertion of said cartridge (8) into said housing (7), a liquid-flow connection is established between said cartridge (8) and said dosing chamber (38).

4. Apparatus according to claim 3, comprising a first duct (19) and a first ball valve (24), said trocar (21) being disposed at a first end of said first duct (19), said first ball (24) being disposed at a second end of said first duct (19) opposite said first end, and said first ball valve (24) being disposed to prevent return of liquid into said cartridge (8).

5. Apparatus according to claim 1, comprising a threaded ring (4) connecting said first (2) and second (3) separable portions of said body.

6. Apparatus according to claim 1, 2, 3, or 4, comprising a second duct (29) which connects said dosing chamber (38) with said injector (36), and a second ball valve (31) subject to the action of a spring (32), said second ball valve (31) being disposed to open upon liquid flow from said dosing chamber (8) through said second duct (29).

7. Apparatus according to claim 6, said injector (36) comprising a material which is abrasion resistant.

8. Apparatus according to claim 6, said working piston (52) comprising a groove (53), said end piece (45) comprising a head (54), and said groove (53) engaging said head (54).

9. Apparatus according to claim 1, 2, 3, or 4, said injector (36) being flat.

10. Apparatus according to claim 9, said working piston (52) comprising a groove (53), said end piece (45) comprising a head (54), and said groove (53) engaging said head (54).

11. Apparatus according to claim 1, 2, 3, or 4, said working piston (52) comprising a groove (53), said end piece (45) comprising a head (54), and said groove (53) engaging said head (54).

12. Apparatus according to claim 1, 2, 3, or 4 comprising a support block (65) and stopping-and-blocking means (66, 73, 75) in said second separable portion (3),
said support block (65) comprising flat seals (77, 78, 79, 80) and being rigidly connected to an inner wall of said second portion (3) of said elongated body by said stopping-and-blocking means (66, 73, 75),
said support block (65) forming a passage (82) which holds said distributor (83) in axially mobile fashion,
said distributor (83) comprising a stepped cylindrical profile (84, 85, 86, 87, 88) which is adapted such that, depending on the position of distributor (83), pneumatic connection is established between said tubing connection (102) and said tight chamber (51) or between said tight chamber (51) and the open air.

13. Apparatus according to claim 12, said support block (65) comprising a prolongation (72), and a first ring (109) being fastened to said prolongation (72),
a second ring (75) being fastened to said second portion (3) of said body,
said first ring (109) comprising a portion having conical shape and extending in part into a cavity (106) formed between said prolongation (72) and said second ring (75), thereby forming a settable slot (107) for regulating pressure discharge from said tight chamber (51).

14. Apparatus according to claim 13, said distributor (83) comprising a bore (100) which slidably comprises a coaxial duct (99) in communication with said tubing connection (102) and with said tight chamber (51), said duct being connected to a clearance (82) between said support block (65) and said distributor (83) by a radial passage (101) formed by said distributor (83).

15. Apparatus according to claim 14, comprising a safety valve (116) which is disposed between said clearance (82) and the open air, a sliding ring (112) on the outside of said motive portion (3) of said body and adapted to operate said safety valve (116),
said sliding ring (112) comprising an inner recess (114) which terminates in a slanting face (115) adapted such that, depending on the axial position of said sliding ring (112), said safety valve (116) is open or closed.

16. Apparatus according to claim 12, said distributor (83) comprising a bore (100) which slidably comprises a coaxial duct (99) in communication with said tubing connection (102) and with said tight chamber (51), said duct being connected to a clearance (82) between said support block (65) and said distributor (83) by a radial passage (101) formed by said distributor (83).

17. Apparatus according to claim 16, comprising a safety valve (116) which is disposed between said clearance (82) and the open air, a sliding ring (112) on the outside of said motive portion (3) of said body and adapted to operate said safety valve (116),
said sliding ring (112) comprising an inner recess (114) which terminates in a slanting face (115) adapted such that, depending on the axial position of said sliding ring (112), said safety valve (116) is open or closed.

18. Apparatus according to claim 12, comprising a return spring (98) which is disposed to apply said distributor (83) against said flat seals (77, 79).

19. Apparatus according to claim 1, 2, 3, or 4 connected to a distribution station of compressed air, said distribution station being controlled by an actuating member which comprises means for stoppage of admission of air to chamber (51), whereby each cycle of movement of said distributor (83) requires reactivation of said actuating member.

20. A needleless liquid injection apparatus which includes an elongate body comprising first and second separable portions,
said first separable portion (202), here also called medical portion, comprising a channel (210) in communication with at least one housing (234) adapted to receive a tight cartridge (235),
said tight cartridge (235) comprising a movable bottom piece (254) and containing a liquid to be injected,
said first separable portion (202) further comprising at least one dosing chamber (243) in communication with said housing (234), and a nozzle (207) in communication with said dosing chamber (243),
said nozzle (207) comprising an injector adapted for forming a narrow liquid jet upon abrupt delivery of said liquid from said dosing chamber (243),
said second separable portion (203), here also called motive portion, comprising a pneumatic connection (286), a tight chamber (287) in communication with said pneumatic connection (286), and an assembly adapted to perform a pneumatically controlled alternating movement,
said assembly comprising
a working-piston first subassembly which comprises a piston (237) disposed between said housing (234) and said nozzle (207), and an end piece (267) disposed between said housing (234) and said tight chamber (287),
a pushing-member second subassembly which is adapted to act on said first subassembly in a first direction, comprising an axial thrust member (276) disposed between said housing (234) and said tight chamber (287), and an elastic membrane (280) disposed between said thrust member (276) and said pneumatic connection (206), thereby delimiting said tight chamber (287),
a control spring (241) disposed within said first separable portion (202) to act on said first subassembly in a second direction which is opposite to said first direction, a temporary connection member (270) disposed within said second separable portion (203) for rigidly connecting said first and second subassemblies while said subassemblies jointly move in said first direction under the influence of pressurization of said tight chamber (287), said temporary connection member (270) being disposed to disengage after movement over a desired distance, thereby permitting said piston (237) to move in second direction by action of said control spring (241).

21. Apparatus according to claim 20, comprising a sleeve (272) connecting said piston (237) and said end piece (267), said temporary connection member (270) comprising a ball, and said sleeve comprising a profiled recess (273) for the escapement of said ball.

22. Apparatus according to claim 21, comprising a chuck (217) which delimits said dosing chamber (243), said piston (237) comprising a coaxial sleeve (233) and being slidably mounted relative said chuck (217), said dosing chamber (243) having an annular shape adapted for dosage of said liquid in a space between said chuck (217) and said coaxial sleeve (233), said chuck (217) comprising an axial channel (218), and said dosing chamber (243) being in communication with said axial channel (218).

23. Apparatus according to claim 22, comprising a trocar (229) which communicates with the inside of said cartridge (235) for authorizing the admission of said liquid to said dosing chamber (243), said axial channel (218) comprising a ball valve (331) in register with said trocar (229), said chuck (217) comprising a radial duct (244) for admission of said liquid to said dosing chamber (243), said ball valve (331) being adapted to interrupt communication with said cartridge (235) during displacement of said piston (237) under the effect of said control spring (241).

24. Apparatus according to claim 23, comprising a blocking lever (247) which, in a first position, immobilizes said coaxial sleeve (233) relative to said chuck (217) and which, in a second position, permits relative motion between said coaxial sleeve (233) and said chuck (217), said second position being assumed upon manual control.

25. Apparatus according to claim 22, comprising a blocking lever (247) which, in a first position, immobilizes said coaxial sleeve (233) relative to said chuck (217) and which, in a second position, permits relative motion between said coaxial sleeve (233) and said chuck (217), said second position being assumed upon manual control.

26. Apparatus according to claim 21, said end piece (267) comprising a prolongation (268) which is axially mobile in said coaxial sleeve (272).

27. Apparatus according to claim 20 or 21, comprising a bearing piston (255) which is adapted to act on said bottom piece (254), a guiding support (257) for said bearing piston (255) within said second separable portion (203), and a spring (258) disposed within said second separable portion (203) to act between said bearing piston (255) and said guiding support (257).

28. Apparatus according to claim 20, comprising means for preventing accidental discharge of liquid, said means comprising a movable plaquette (301) disposed within said first separable portion (202), a push button (298) on said first separable portion (202) and disposed to act on said plaquette (301), and a spring (299) disposed within said first separable portion (202) to counteract the action of said push button (298), said plaquette (301) comprising a passage (302) which is in alignment with said channel (210) only when said push button is depressed against said spring.

29. Apparatus according to claim 20, comprising means for preventing accidental discharge of liquid, said means comprising a locking plunger (315) which is disposed in said channel (210), a sliding thumb-piece (322) on an outer surface of said body, a radial pin (311) disposed between said thumb-piece (322) and said plunger (315), and a spring (312) disposed to act on said pin (311) in a radially outward direction, said pin (311) being adapted to hold said plunger (315) in a blocking position when said thumb-piece (322) is in a first position, and to release said plunger (315) when said thumb-piece (322) is in a second position.

30. Apparatus according to claim 29, said means for preventing accidental discharge of liquid comprising a sliding thumb piece (322) on said first separable portion (202) and a spring member (328) attached to said thumb piece, said first separable portion (202) comprising a shoulder (327) for engaging said spring member (328).

31. Apparatus according to claim 20, said piston (237) having the shape of a sleeve and comprising a shoulder (240) which is disposed to be acted upon by said control spring (241).

* * * * *